United States Patent
Sharif

(10) Patent No.: US 6,344,477 B1
(45) Date of Patent: Feb. 5, 2002

(54) PROSTAGLANDIN E AGONISTS FOR TREATMENT OF DRY EYE

(75) Inventor: Najam A. Sharif, Arlington, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/462,737

(22) Filed: Jan. 12, 2000

Related U.S. Application Data

(60) Provisional application No. 60/113,698, filed on Dec. 24, 1998.

(51) Int. Cl.$^7$ ............................................. A67K 31/215
(52) U.S. Cl. ......................... 514/530; 514/573; 514/912
(58) Field of Search ................................. 514/530, 573, 514/912

(56) References Cited

U.S. PATENT DOCUMENTS

| | | |
|---|---|---|
| 3,991,759 A | 11/1976 | Urquhart |
| 4,131,651 A | 12/1978 | Shah et al. |
| 4,370,325 A | 1/1983 | Packman |
| 4,388,324 A | 6/1983 | Horrobin |
| 4,409,205 A | 10/1983 | Shively |
| 4,744,980 A | 5/1988 | Holly |
| 4,753,945 A | 6/1988 | Gilbard et al. |
| 4,818,537 A | 4/1989 | Guo |
| 4,868,154 A | 9/1989 | Gilbard et al. |
| 4,883,658 A | 11/1989 | Holly |
| 4,914,088 A | 4/1990 | Glonek et al. |
| 4,966,773 A | 10/1990 | Gressel et al. |
| 5,041,434 A | 8/1991 | Lubkin |
| 5,075,104 A | 12/1991 | Gressel et al. |
| 5,151,444 A | 9/1992 | Ueno et al. |
| 5,290,572 A | 3/1994 | MacKeen |
| 5,294,607 A | 3/1994 | Glonek et al. |
| 5,403,841 A | 4/1995 | Lang et al. |
| 5,455,265 A | 10/1995 | Chandraratna |
| 5,620,921 A | 4/1997 | Sullivan |
| 5,658,897 A | 8/1997 | Burk |
| 5,658,948 A | 8/1997 | Lucero |
| 5,696,166 A | 12/1997 | Yanni et al. |
| 5,741,810 A | 4/1998 | Burk |

FOREIGN PATENT DOCUMENTS

| | | |
|---|---|---|
| EP | 561073 A1 | 9/1993 |
| WO | WO 97/31895 | 9/1997 |

OTHER PUBLICATIONS

Horrobin, "Essential fatty acid metabolism in diseases of connective tissue with special reference to scleroderma and to Sjogren's syndrome" Med. Hypotheses 14(3):233–497 (1984), Database Accession No. 101:128381 XP002143256 abstract.

Abe et al., "3,4,5–Trimethoxy–N–3(3–piperidyl) benzamide (KU–54)," Pharmacomet, 27(3):521–531 (1984).

Adami et al., "Pharmacological research on gefarnate, a new synthetic isoprenoid with anti-ulcer action," *Archives of International Pharmacodynamics*, 147(1–2):113–145 (1964).

Chomczynski and Sacchi, "Single–Step method of RNA isolation by acid guanidinium thiocyanate–phenol–chloroform extraction," *Analytical Biochemistry*, 162:156–159 (1987).

Coleman et al., "VIII. International Union of Pharmacology classification of prostanoid receptors: Properties, distribution, and struture of the receptors and their subtypes," *Pharmacological Reviews*, 46(2):205–229 (1994).

Crider et al., "Prostaglandin–stimulated adenylyl cyclase activity via a pharmacologically defined $EP_2$ receptor in human non–pigmented ciliary epithelial cells," *J. Ocular Pharmacology & Therapeutics*, 14(4):293–304 (1998).

Crider et. al., "Use of a semi–automated, robotic radioimmunoassay to measure cAMP generated by activation of DP–, $EP_2$–, and IP–prostaglandin receptors in human ocular and other cell–types," *Prostaglandins, Leukotrienes & Essential Fatty Acids*, 59(1):77–82 (1998).

Dartt et al., "Localization of nerves adjacent to goblet cells in rat conjunctiva," *Current Eye Research*, 14(11):993–1000 (1995).

Dartt et al., "Vasoactive intestinal peptide–stimulated glycocongjugate secretion from conjunctival goblet cells," *Exp. Eye Res.*, 63:27–33 (1996).

Dilly et al., "Surface Changes in the Anaesthetic Conjunctiva in Man, with Special Reference to the Production of Mucus from a Non–Goblet–Cell Source," *British Journal of Ophthalmology*, 65:833–842 (1981).

Gilbard, "Dry eye: pharmacological approaches, effects, and progress," *The CLAO Journal*, 22(2):141–145 (1996).

Gipson and Inatomi, "Mucin genes expressed by ocular surface epithelium," *Progress in Retinal and Eye Research*, 16(1):81–98 (1997).

Greiner et al., "Mucus Secretory Vesicles in Conjunctival Epithelial Cells of Wearers of Contact Lenses," *Archives of Ophthalmology*, 98:1843–1846 (1980).

Hassan et al., "Presence of prostaglandin $EP_4$ receptor gene expression in a rat gastric mucosal cell line," *Digestion*, 57:196–200 (1996).

Lemp, Report of the National Eye Institute/Industry Workshop on Clinical Trials in Dry Eyes, *"The CLAO Journal,"* 21(4):221–231 (1995).

Milne et. al., "Human monocytes and cultured CHO cells both express $EP_4$ receptors positively coupled to adenylate cyclase," *Br. J. Pharmacology*, 113 (Supp):8 (1994).

(List continued on next page.)

Primary Examiner—Zohreh Fay
(74) Attorney, Agent, or Firm—Barry L. Copeland

(57) ABSTRACT

Compositions and methods for the treatment of dry eye and related diseases utilizing $EP_4$ receptor agonists are disclosed.

10 Claims, No Drawings

OTHER PUBLICATIONS

Nakmura et al., "Gefarnate stimulates secretion of mucin–like glycoproteins by corneal epithelium in vitro and protects corneal epithelium from desiccation in vivo," *Experimental Eye Research,* 65:569–574 (1997).

Schein et al., "Prevalence of dry eye among the elderly," *American J. Ophthalmology,* 124:723–738 (1997).

Senchyna and Crankshaw, "Use of reverse transcription–polymerase reaction to identify prostanoid receptor mRNA in human myometrium," *British J. Pharmacology,* 116:280 (1995).

Sharif et al., "Pharmacological analysis of mast cell mediator and neurotransmitter receptors coupled to adenylate cyclase and phospholipase C on immunocytochemically–defined human conjunctival epithelial cells," *J. Ocular Pharmacology & Therapeutics,* 13(4):321–336 (1997).

Watanabe et al., "Human Corneal and Conjuctival Epithelia Produce a Mucin–Like Glycoprotein for the Apical Surface," *Investigative Ophthalmology and Visual Science (IOVS),* 36(2):337–344 (1995).

Yanni et al, "Effect of Intravenously Administered Lipoxygenase Metabolites on Rat Tracheal Mucous Gel Layer Thickness," *International Archives of Allergy and Applied Immunology,* 90:307–309 (1989).

PROSTAGLANDIN E AGONISTS FOR TREATMENT OF DRY EYE

This application is a 371 of the PCT/US99/29734 filed on Dec. 14, 1999, which claims the benefit of Ser. No. 60/113,688, filed Dec. 24, 1998.

FIELD OF THE INVENTION

The present invention relates to the use of $EP_4$-receptor agonists and partial agonists to stimulate mucin secretion to treat dry eye, keratoconjunctivitis, Sjogren's syndrome and related ocular surface diseases.

BACKGROUND OF THE INVENTION

Dry eye is a common ocular surface disease afflicting millions of people in the U.S. each year, especially the elderly (Schein et al., Prevalence of dry eye among the elderly. *American J. Ophthalmology*, 124:723–738, (1997)). Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricialpemphigoid manifest dry eye complications.

Although it appears that dry eye may result from a number of unrelated pathogenic causes, the common end result is the breakdown of the tear film, which results in dehydration of the exposed outer surface of the eye. (Lemp, Report of the Nation Eye Institute/Industry Workshop on Clinical Trials in Dry Eyes, *The CLAO Journal*, 21(4):221–231 (1995)). Four events have been identified which singly or in combination are believed to result in the dry eye condition: a) decreased tear production or increased tear evaporation; b) decreased conjunctival goblet-cell density; c) increased corneal desquamation; and d) destabilization of the cornea-tear interface (Gilbard, Dry eye: pharmacological approaches, effects, and progress. *The CLAO Journal*, 22:141–145 (1996)). Another major problem is the decreased mucin production by the conjunctival cells and/or corneal epithelial cells of mucin, which protects and lubricates the ocular surface (Gipson and Inatomi, Mucin genes expressed by ocular surface epithelium. *Progress in Retinal and Eye Research*, 16:81–98 (1997)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.) and U.S. Pat. No. 5,294,607 (Glonek et al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate tear film; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjuctival epithelium of human eyes (Greiner et al., Mucus Secretory Vesicles in Conjunctival Epithelial Cells of Wearers of Contact Lenses, *Archives of Ophthalmology*, 98:1843–1846 (1980); and Dilly et al., Surface Changes in the Anaesthetic Conjunctiva in Man, with Special Reference to the Production of Mucus from a Non-Goblet-Cell Source, *British Journal of Ophthalmology*, 65:833–842 (1981)). A number of human-derived mucins which reside in the apical and subapical corneal epithelium have been discovered and cloned (Watanabe et al., Human Corneal and Conjuctival Epithelia Produce a Mucin-Like Glycoprotein for the Apical Surface, *Investigative Ophthalmology and Visual Science (IOVS)*, 36(2):337–344 (1995)). Recently, a new mucin was reported to be secreted via the cornea apical and subapical cells as well as the conjunctival epithelium of the human eye (Watanabe et al., *IOVS*, 36(2):337–344 (1995)). These mucins provide lubrication, and additionally attract and hold moisture and sebacious material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, Effect of intravenously Administered Lipoxygenase Metabolites on Rat Tracheal Mucous Gel Layer Thickness, *International Archives of Allergy And Applied Immunology,* 90:307–309 (1989)).

The conventional treatment for dry eye, as discussed above, includes administration of artificial tears to the eye several times a day. Other agents claimed for increasing ocular mucin and/or tear production include vasoactive intestinal polypeptide (Dartt et al. Vasoactive intestinal peptide-stimulated glycocongiugate secretion from conjunctival goblet cells. *Experimental Eye Research,* 63:27–34, (1996)), gefarnate (Nakmura et al. Gefarnate stimulates secretion of mucin-like glycoproteins by corneal epithelium in vitro and protects corneal epithelium from dessication in vivo, *Experimental Eye Research,* 65:569–574 (1997)), and the use of liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), retinoids (U.S. Pat. No. 5,455,265) and hydroxyeicosatetraenoic acid derivatives (U.S. Pat. No. 5,696,166). However, many of these compounds or treatments suffer from a lack of specificity, efficacy and potency and none of these agents have been marketed so far as therapeutically useful products to treat dry eye and related ocular surface diseases. Thus, there remains a need for an efficacious therapy for the treatment of dry eye and related diseases.

Additionally, in the gastric mucosal cell-type, prostaglandin $E_2$ ($PGE_2$) has been shown to stimulate mucin secretion via the $EP_4$ receptor-subtype and the mRNA for this receptor has been demonstrated in the gastric mucosal cells (Hassan et al. Presence of prostaglandin $EP_4$ receptor gene expression in a rat gastric mucosal cell line, *Digestion,* 57:196–200 (1996)); Adami et al. Pharmacological research on gefarnate, a new synthetic isoprenoid with anti-ulcer action. *Archives of International Pharmacodynamics.* 147:113–145 (1964)).

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (U.S. Pat. No. 5,151,444; EP 0 561 073 A1; Coleman et al., VIII International Union of Pharmacology classification of prostanoid receptors: Properties, distribution, and structure of the receptors and their subtypes, *Pharmacological Reviews,* 45:205–229 (1994)). Depending on the number of double-bonds in the α-(top chain) and/or the ω-chain (bottom chain), the prostaglandins are further classified with subscripts such as $PGD_2$, $PGE_1$, $PGE_2$, $PGF_{2\alpha}$, etc. (U.S. Pat. No. 5,151,444; Coleman et al., VIII International Union of Pharmacology classification of prostanoid receptors: Properties, distribution, and structure of the receptors and their subtypes, *Pharmacological Reviews,* 45:205–229 (1994)). Whilst these classes of prostaglandins interact preferably with the designated major classes of receptors (e.g. DP, EP, FP) and subclasses of receptors (e.g. $EP_2$, $EP_3$, $EP_4$), the subscripts associated with the prostaglandin does not necessarily correspond with the subclass of the receptor(s) with which they interact. Furthermore, it is well known that these endogenous prostaglandins are non-specific in terms of interacting with the various classes of prostaglandin receptors. Thus, $PGE_2$ not only interacts with $EP_2$ receptors, but can also activate $EP_1$, $EP_2$, $EP_3$ and $EP_4$ receptors (Coleman et al., VIII International Union of Pharmacology classification of prostanoid receptors: Properties, distribution, and structure of the receptors and their subtypes, *Pharmacological Reviews,* 45:205–229 (1994)). Of interest in the present invention are prostaglandins which are believed to exhibit mucin-producing activity and are based on the structure of $PGE_2$ (an E-series prostaglandin):

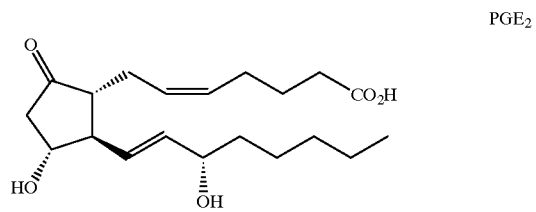

$PGE_2$

The $EP_4$ prostaglandin receptor belongs to a family of prostaglandin receptors, all of which have seven-transmembrane domains and couple to specific G-proteins. When the $EP_4$ receptor on the cell surface is activated by the binding of a specific agonist ligand (a prostaglandin belonging to one of several defined classes of prostaglandins) the conformation of the G-protein is modified to favor the coupling to the enzyme adenylate cyclase (inside the cell). This event then leads to the hydrolysis of ATP to generate the intracellular second messenger cyclic AMP (cAMP) (Coleman et al., VIII International Union of pharmacology classification of prostanoid receptors: Properties, distribution, and structure of the receptors and their subtypes, *Pharmacological Reviews,* 45:205–229 (1994)). The cAMP produced in this manner then leads to the activation of various cAMP-dependent enzymes which produce various biochemical events leading to the final biological response which may involve tissue contraction, hormone release or fluid and /or electrolyte secretion amongst other responses.

We have now unexpectedly discovered $EP_4$ receptor mRNA in human primary and immortalized corneal epithelial (CEPI) cells. We previously detected functional EP4 receptors in human conjunctival epithelial cells (Sharif et al., Pharmacological analysis of mast cell mediator and neurotransmitter receptors coupled to adenylate cyclase and phospholipase C on immunocytochemically-defined human conjunctival epithelial cells. *J. Ocular Pharmacology & Therapeutics,* 13, 321–336 (1997)), and appreciate that both human corneal epithelial cells (Gipson and Inatomi, Mucin genes expressed by the ocular surface epithelium. *Progress in Retinal and Eye Research,* 16:81–98 (1997)) and conjunctival cells (Dartt et al. Localization of nerves adjacent to goblet cells in rat conjunctiva. *Current Eye Research,* 14:993–1000 (1995)) are capable of secreting mucins. Hence, the discovery of the presence of $EP_4$ receptors in human corneal and conjunctival epithelial cells prompted us to theorize that a selective $EP_4$ agonist might provide a useful therapy for dry eye.

SUMMARY OF THE INVENTION

The present invention is directed to compositions and methods for the treatment of dry eye and other disorders requiring the wetting of the eye. More specifically, the present invention discloses compositions containing $EP_4$ receptor agonists and methods for treating dry eye type disorders.

Preferred compositions include an effective amount of an $EP_4$ receptor agonist for the production of mucins in mammals, and especially in humans. The compositions are administered topically to the eye for the treatment of dry eye.

DETAILED DESCRIPTION OF THE INVENTION

It has now been discovered that certain $EP_4$ receptor agonists stimulate mucin production in human conjuctival epithelium and are therefore believed to be useful in treating dry eye. As used herein, the term "$EP_4$ receptor agonists" refers to any compound which acts as an agonist or partial agonist at the $EP_4$ receptor, thereby stimulating mucin production and/or secretion in the conjunctival epithelium and goblet cells following topical ocular application. Specifically included in such definition are compounds of the following formula I:

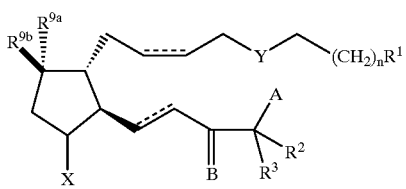

wherein:
$R^1 = CO_2R$, $CONR^4R^5$, or $CH_2OR^6$, where:
    R=H or pharmaceutically acceptable cationic salt moiety, or $CO_2R$=pharmaceutically acceptable ester moiety;
    $R^4$, $R^5$=same or different=H or alkyl; and
    $R^6$=H, acyl, or alkyl;
n=0 or 2;
Y=O, S, or $CH_2$;
one of $R^{9a}$, $R^{9b}$=H and the other=$OR^7$, where $R^7$=H, alkyl, or acyl; or, $R^{9b}R^{9a}$ taken together=O as a carbonyl;
X=H, Cl, F, or $OR^8$ in either configuration, where $R^8$=H, alkyl, or acyl;
B=O, or H and $OR^{10}$ in either configuration, where $R^{10}$=H, alkyl, or acyl;
═══════=single or double bond;
$R^2$, $R^3$=same or different=H or alkyl, or $R^2$, $R^3$ may be combined to form a $C_3$–$C_7$ cycloalkyl;
A=H, $C_2$–$C_6$ alkyl, $C_3$–$C_7$ cycloalkyl, $(CH_2)_{n'}D$, $(CH_2)_{n'}OD$, where:
    n'=1–4; and
D=

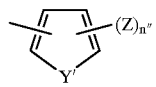

wherein:
n"=0–3;
Z=H, halogen, $C_1$–$C_4$ alkyl, $C_1$–$C_4$ alkoxy, or $CF_3$; and
Y'=CH═CH, O, or S;
with the proviso that when $R_2$–$R_3$ form a cycloalkyl, then A=H;
with the further provisos that (1) when $R^{9a}R^{9b}$=O as a carbonyl, then X=H or $OR^8$ in either configuration and A≠$(CH_2)_{n'}D$ or $(CH_2)_{n'}OD$; and (2) when one of $R^{9a}$, $R^{9b}$=H and the other=$OR^7$, then $R^2$=$R^3$=H and A=$(CH_2)_{n'}D$ or $(CH_2)_{n'}OD$.

As used herein, the terms "pharmaceutically acceptable ester"/"pharmaceutically acceptable cationic salt" means any ester/cationic salt that would be suitable for therapeutic administration to a patient by any conventional means without significant deleterious health consequences; and "ophthalmically acceptable ester"/"ophthalmically acceptable cationic salt" means any pharmaceutically acceptable ester/cationic salt that would be suitable for ophthalmic application, i.e. non-toxic and non-irritating. Wavy line attachments indicate that the configuration may be either alpha (α) or beta (β). The carbon numbering is as indicated in formula I, even when n=2. Dashed lines on bonds [e.g., between carbons 4 (C-4) and 5 (C-5)] indicate a single or double bond. Two solid lines present specify the configuration of the relevant double bond. Hatched lines indicate the α configuration. A solid triangular line indicates the β configuration.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred for purposes of the present invention are those compounds of formula I, wherein:
$R^1$=$CO_2R$, $CONR^4R^5$, or $CH_2OR^6$, where:
  R=H, lower alkyl, or ophthalmically acceptable salt moiety;
  $R^4$=$R^5$=H; and
  $R^6$=H or lower alkyl;
n=0;
Y=$CH_2$;
$R^{9a}$=OH, and $R^{9b}$=H;
X=OH in the α configuration;
B=H in the β configuration and $OR^{10}$ in the α configuration, where $R^{10}$=H or $CH_3$;
$R^2$=$R^3$=H;
A=$(CH_2)_{n'}$D or $(CH_2)_{n'}$OD, where:
  n'=1–4; and
  D=

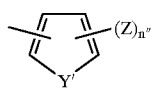

wherein:
  n"=0–3;
  Z=H, Cl, Br, methyl, methoxy, or $CF_3$; and
  Y'=CH=CH, O, or S.

Also preferred for purposes of the present invention are those compounds of formula I, wherein:
$R^1$=$CO_2R$, $CONR^4R^5$, or $CH_2OR^6$, where
  R=H, lower alkyl, or ophthalmically acceptable cationic salt moiety;
  $R^4$=$R^5$=H; and
  $R^6$=H or lower alkyl;
n=0;
Y=$CH_2$;
$R^{9a}R^{9b}$=O as a carbonyl;
X=H, or OH in the α configuration;
━━━━━━ = single or double bond;
B=H in the β configuration and OH in the α configuration;
$R^2$=$R^3$=H or $CH_3$; and
A=n-butyl.

Examples of most preferred compounds are the following: 11-deoxy-$PGE_1$, 11-deoxy-16,16,-dimethyl-$PGE_2$, 16,16-dimethyl-$PGE_2$ [all of which are commercially available from Cayman Chemical Co (Ann Arbor, Mich.)] as well as the following prostaglandin analogs disclosed in WO 97/31895: 7-[3α,5α-dihydroxy-2-(3αhydroxy-5-(5-(2,3-dibromo)thienyl)-1E-pentenyl)cyclopentyl]-5Z-heptenoic acid; 7-[3α,5α-dihydroxy-2-(3α-hydroxy-5-(2-methyl)furanyl-1E-pentenyl) cyclopentyl]-5Z-heptenoic acid; 7-[3α,5α-dihydroxy-2-(3α-hydroxy-5-(5-(2,3-dibromo) thienyl)-1E -pentenyl)cyclopentyl]-5Z-heptenamide; 7-[3α, 5α-dihydroxy-2-(3α-methoxy-5-(2-furanyl)-1E-pentenyl) cyclopentyl]-5Z-heptenoic acid; and 7-[3α,5α-dihydroxy-2-(3α-methoxy-5-(3-(2-methyl)thienyl-1E-pentenyl) cyclopentyl]-5Z-heptenoic acid. The entire disclosure of WO 97/31895 relative to the foregoing compounds is incorporated herein by this reference. Although the free acids of the above mentioned compounds, and other $EP_4$ agonists/partial agonists, would be the active agents eliciting the beneficial effects at $EP_4$ receptor, the use of esters and other derivatives of the compounds are also encompassed in the present invention.

EXAMPLE 1

Immortalized human non-pigmented ciliary epithelial cells (containing $EP_2$ receptors) and Chinese hamster ovary cells (containing $EP_4$ receptors) were stimulated with various prostaglandins for 15–60 min at 23° C. The cAMP produced by receptor activation was determined by a specific radioimmunoassay as previously described (Sharif et. al., Pharmacological analysis of mast cell mediator and neurotransmitter receptors coupled to adenylate cyclase and phospholipase C on immunocytochemically-defined human conjunctival epithelial cells, *J. Ocular Pharmacology & Therapeutics,* 13:321–336 (1997); Crider et. al., Prostaglandin-stimulated adenylyl cyclase activity via a pharmacologically-defined $EP_2$ receptor in human non-pigmented epithelial cells, *J. Ocular Pharmacology & Therapeutics,* 14:293–304 (1998); Crider et. al., Use of a semi-automated, robotic radioimmunoassay to measure cAMP generated by activation of DP-, $EP_2$- and IP-prostaglandin receptors in human ocular and other cell-types, *Prostaglandins, Leukotrienes & Fatty Acids,* 59:77–82 (1998); Milne et. al., Human monocytes and cultured Chinese hamster ovary cells express $EP_4$ receptors positively coupled to adenylate cyclase, *Br. J. Pharmacology,* 113 (supplement), 8p, (1994)). The dose-response curves for the prostaglandins were analyzed with an iterative, non-linear curve-fitting computer program to generate the relative potencies ($EC_{50}$; concentration of the compound which produces 50% of the maximal response) of the compounds. The smaller the $EC_{50}$ value the more potent the compound. Thus, as can be seen in Table 1 below, certain compounds were significantly more potent agonists at the $EP_4$ receptor than at the $EP_2$ receptor, making them relatively "$EP_4$-selective". On the other hand, butaprost and ZK118182 were more $EP_2$-selective compounds, whilst cloprostenol and fluprostenol ($EP_3$—/FP-selective) were inactive at the $EP_2$ and $EP_4$ receptors.

TABLE 1

Potency and Efficacy of Selected Prostaglandins at the $EP_2$ and $EP_4$ Receptor Subtypes.

| Prostaglandins and Preferred Receptor Activation | Potency ($EC_{50}$, nM) at $EP_2$ Receptors in Immortalized Human Non-pigmented Ciliary Epithelial Cells | Potency ($EC_{50}$, nM) at $EP_4$ Receptors in Chinese Hamster Ovary Cells |
|---|---|---|
| $PGE_2$ (non-selective) | 38 nM (100% efficacy) | 35 nM (100% efficacy) |
| 11-deoxy-$PGE_1$ | 500 nM (100% efficacy) | 38 nM (86% efficacy) |
| 16,16-dimethyl-$PGE_2$ | 686 nM (97% efficacy) | 31 nM (100% efficacy) |
| 11-deoxy-16,16-dimethyl-$PGE_2$ | 739 nM (75% efficacy) | 176 nM (99% efficacy) |
| ZK118182 (DP-selective agonist) | 700 nM (44% efficacy) | >10,000 nM |
| Butaprost ($EP_2$-selective agonist) | 212 nM (55% efficacy) | >10,000 nM |
| Fluprostenol (FP-selective agonist) | Inactive | Inactive |
| Cloprostenol (FP/$EP_3$-selective agonist) | Inactive | Inactive |

EXAMPLE 2

Table 2. RT-PCR Data Demonstrating the Presence of $EP_4$ Receptor mRNAs in the Human Ocular Cells Total ribonucleic acid (RNA) was isolated from cells of interest using the well known guanidine thiocyanate-phenol-chloroform extraction procedure (Chomczynski and Sacchi, *Analytical Biochemistry*, 162: 156–163 (1987)). The isolated RNA was reverse transcribed into complementary DNA (cDNA) using the well known protocol outlined in the GeneAmp RNA PCR kit (Perkin Elmer/Cetus, Norwalk, Conn). The technique of reverse transcriptase polymerase chain reaction (RT-PCR) using oligonucleotide primers for the different human prostaglandin receptors was employed to detect the messenger RNAs (mRNAs) for various prostaglandin receptors in primary and immortalized human corneal epithelial, choroidal and iridial melanocytes as previously described (Senchyna and Crankshaw, Use of reverse transcription-polymerase chain reaction to identify prostanoid receptor mRNA in human myometrium, *British J. Pharmacology*, 116:280 (1995)). As can be seen in Table 2 below, whilst the corneal epithelial cells expressed the $EP_4$ receptor mRNA, the negative control cells (human choroidal and iridial melanocytes) did not express this receptor mRNA.

TABLE 2

RT-PCR data demonstrating the presence of $EP_4$ receptor mRNAs in the human ocular cells

| Cell Types | Detection of $EP_4$ Receptor mRNA (number of times $EP_4$ mRNA successfully detected in various cell lysates from 2 experiments) |
|---|---|
| Primary human corneal epithelial cells (donor # 421-97) | 2/2 |
| Primary human corneal epithelial cells (donor # 575-97) | 2/2 |
| Immortalized human corneal epithelial cells (CEPI-17-CL4) | 2/2 |
| Human choroidal melanocytes (line A08) | 0/2 |
| Human iridial melanocytes (line A47) | 0/2 |

The $EP_4$ agonists of the present invention may be contained in various types of pharmaceutical compositions, in accordance with formulation techniques known to those skilled in the art. In general, the $EP_4$ agonists will be formulated in solutions for topical ophthalmic administration. Solutions, suspensions and other dosage forms are particularly preferred for the treatment of dry eye.

The ophthalmic compositions of the present invention will include one or more $EP_4$ agonists in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the $EP_4$ agonists may also be readily incorporated into other types of compositions, such as suspensions, viscous or semi-viscous gels, or other types of solid or semi-solid compositions. Suspensions may be preferred for esterified $EP_4$ agonists which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the $EP_4$ agonists from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one $EP_4$ agonist of the present invention.

The invention in its broader aspects is not limited to the specific details shown and described above. Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis;* J. D. Morrison and J. W. Scott, Eds.; Academic Press Publishers: New York, 1983–1985, volumes 1–5; *Principles of Asymmetric Synthesis;* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC;* G. Subramanian, Ed.; VCH Publishers: New York, 1994; *Chiral Separations by HPLC;* A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions,* volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for the treatment of dry eye in mammals comprising administering to an affected eye, a pharmaceutically effective amount of an $EP_4$ receptor agonist according to formula I:

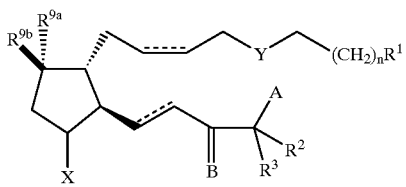

wherein:
$R^1 = CO_2R$, $CONR^4R^5$, or $CH_2OR^6$, where:
  R=H or pharmaceutically acceptable cationic salt moiety, or $CO_2R$=pharmaceutically acceptable ester moiety;
  $R^4$, $R^5$=same or different=H or alkyl, and
  $R^6$=H, acyl, or alkyl;
n=0 or 2;
one of $R^{9a}$, $R^{9b}$=H and the other=$OR^7$, where $R^7$=H, alkyl, or acyl; or, $R^{9b}R^{9a}$ taken together=O as a carbonyl;
X=H, Cl, F, or $OR^8$ in either configuration, where $R^8$=H, alkyl, or acyl;

B=O, or H and $OR^{10}$ in either configuration, where $R^{10}$=H, alkyl, or acyl;
- - - - =single or double bond;
$R^2$, $R^3$=same or different=H or alkyl, or $R_2$, $R_3$ may be combined to form a $C_3$–$C_7$ cycloalkyl;
A=H, $C_2$–$C_6$ alkyl, $C_3$–$C_7$ cycloalkyl, $(CH_2)_{n'}$D, $(CH_2)_{n'}$OD, where:
  n'=1–4; and
D=

wherein:
n"=0–3;
Z=H, halogen, $C_1$–$C_4$ alkyl, $C_1$–$C_4$ alkoxy, or $CF_3$; and
Y'=CH=CH, O, or S;

with the proviso that when $R_2$–$R_3$ form a cycloalkyl, then A=H;

with the further provisos that:
  when $R^{9a}R^{9b}$=O as a carbonyl, then X=H or $OR^8$ in either configuration and A≠$(CH_2)_{n'}$D or $(CH_2)_{n'}$OD;
  when one of $R^{9a}$, $R^{9b}$=H and the other=$OR^7$, then $R^2$=$R^3$=H and A=$(CH_2)_{n'}$D or $(CH_2)_{n'}$OD; and
  $PGE_1$ and $PGE_2$ are excluded.

2. The method of claim 1, wherein for formula I:
$R^1$=$CO_2R$, $CONR^4R^5$, or $CH_2OR^6$, where:
  R=H, lower alkyl, or ophthalmically acceptable salt moiety;
  $R^4$=$R^5$=H; and
  $R^6$=H or lower alkyl;
n=0;
Y=$CH_2$;
$R^{9a}$=OH, and $R^{9b}$=H;
X=$OH^8$ in the α configuration;
B=H in the β configuration and $OR^{10}$ in the α configuration, where $R^{10}$=H or $CH_3$;
$R^2$=$R^3$=H;
A=$(CH_2)_{n'}$D or $(CH_2)_{n'}$OD, where:
  n'=1–4; and
D=

wherein:
n"=0–3;
Z=H, Cl, Br, methyl, methoxy, or $CF_3$; and
Y'=CH=CH, O, or S.

3. The method of claim 2, wherein the $EP_4$ receptor agonist is selected from the group consisting of 7-[3α,5α-dihydroxy-2-(3α-hydroxy-5-(5-(2,3-dibromo)thienyl)-1E-pentenyl)cyclopentyl]-5Z-heptenoic acid;
7-[3α,5α-dihydroxy-2-(3α-hydroxy-5-(2-methyl)furanyl-1E-pentenyl) cyclopentyl]-5Z-heptenoic acid;
7-[3α,5α-dihydroxy-2-(3α-hydroxy-5-(5-(2,3-dibromo)thienyl)-1E-pentenyl)cyclopentyl]-5Z-heptenamide;

7-[3α,5α-dihydroxy-2-(3α-methoxy-5-(2-furanyl)-1E-pentenyl)cyclopentyl]-5Z-heptenoic acid; and 7-[3α,5α-dihydroxy-2-(3α-methoxy-5-(3-(2-methyl)thienyl-1E-pentenyl)cyclopentyl ]-heptenoic acid. 5Z -heptenoic acid.

4. The method of claim 1, wherein for formula I:

$R^1$=$CO_2R$, $CONR^4R^5$, or $CH_2OR^6$, where

R=lower alkyl, or ophthalmically acceptable cationic salt moiety;

$R^4$=$R^5$=H; and $R^6$=H or lower alkyl;

n=0;

Y=$CH_2$;

$R^{9a}R^{9b}$=O as a carbonyl;

X=H, or OH in the α configuration;

⎯⎯⎯⎯⎯=single or double bond;

B=H in the α configuration and OH in the β configuration;

$R^2$=$R^3$=H or $CH_3$; and

A=n-butyl.

5. The method of claim 4, wherein the $EP_4$ receptor agonist is selected from the group consisting of: 11-deoxy-$PGE_1$, 11-deoxy-16,16, dimethyl-$PGE_2$ and 16,16-dimethyl-$PGE_2$.

6. The method of claim 1, wherein the administration to the affected eye is topical, and the concentration of the $EP_4$ receptor agonist is from about 0.001 to about 1.0% w/v.

7. The method of claim 2, wherein the administration to the affected eye is topical, and the concentration of the $EP_4$ receptor agonist is from about 0.001 to about 1.0% w/v.

8. The method of claim 4, wherein the administration to the affected eye is topical, and the concentration of the $EP_4$ receptor agonist is from about 0.001 to about 1.0% w/v.

9. The method of claim 4, wherein the administration to the affected eye is topical, and the concentration of the $EP_4$ receptor agonist is from about 0.001 to about 1.0% w/v.

10. The method of claim 5, the administration to the affected eye is topical, and the concentration of the $EP_4$ receptor agonist is from about 0.001 to about 1.0% w/v.

* * * * *